United States Patent [19]

Broger

[11] Patent Number: 4,544,770

[45] Date of Patent: Oct. 1, 1985

[54] CATALYTIC HYDROGENATION

[75] Inventor: Emil A. Broger, Magden, Switzerland

[73] Assignee: Hoffmann-La Roche Inc., Nutley, N.J.

[21] Appl. No.: 512,845

[22] Filed: Jul. 11, 1983

[30] Foreign Application Priority Data

Jul. 16, 1982 [CH] Switzerland ............... 4359/82
May 16, 1983 [CH] Switzerland ............... 2637/83

[51] Int. Cl.⁴ ............................................. C07F 9/54
[52] U.S. Cl. ...................................... 568/9; 568/11
[58] Field of Search ................................. 568/9, 11

[56] References Cited

U.S. PATENT DOCUMENTS

| | | | |
|---|---|---|---|
| 2,842,599 | 7/1958 | Isler et al. | 568/9 X |
| 3,408,414 | 10/1968 | Surmatis | 568/9 X |
| 3,466,331 | 9/1969 | Surmatis et al. | 568/11 |
| 3,624,105 | 11/1971 | Surmatis et al. | 568/9 X |
| 3,975,445 | 8/1976 | Kienzle et al. | 568/11 |
| 4,045,476 | 8/1977 | Rosenberger | |
| 4,088,689 | 5/1978 | Rosenberger | 568/11 |
| 4,204,073 | 5/1980 | Kienzle | 568/11 X |

OTHER PUBLICATIONS

Chem. Abstracts 89 43855n (1978).
Loeber, et al., Journal Chemical Society (c) 1971, 404.
Pfander, et al., Helv. Chim, Acta 63, 1377 (1980).
H. Pommer, Angew, Chem., 72, 811 (1960).
H. Pommer, Angew, Chem., 72, 911 (1960).
P. Beck, G. M. Kosolapoff, Organo-Phosphorus Compounds 2, 203 (1972).
Bravo, et al., Gazz. Chim., Ital. 106, 743 (1976).
Ford, et al., Org. Chem., 26, 1433 (1961).
Ramirez, et al., J. Amer. Chem. Soc. 79, 6167 (1957).

*Primary Examiner*—Helen M. S. Sneed
*Attorney, Agent, or Firm*—Jon S. Saxe; Bernard S. Leon; George W. Johnston

[57] ABSTRACT

Compounds of the formula:

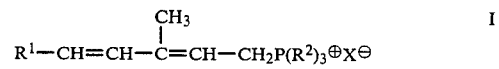

wherein $R^1$ is a 2,6,6-trimethyl-1-cyclohexen-1-yl or 2,3,6-trimethylphenyl group, either of which may be unsubstituted or substituted by a hydroxy group or a protected hydroxy group, $R^2$ is aryl, and $X^-$ is an anion are manufactured by hydrogenating a compound of the formula:

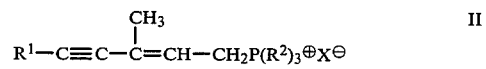

wherein $R^1$, $R^2$ and $X^\ominus$ are as above, in an organic solvent or aqueous-organic solvent in the presence of a nickel-, palladium-, platinum-, cobalt-, rhodium-, iridium-, or ruthenium-containing catalyst.

The process is suitable as an intermediate step in carotenoid and retinoid syntheses.

24 Claims, No Drawings

CATALYTIC HYDROGENATION

BACKGROUND OF THE INVENTION

Field of the Invention

The present invention concerns a novel process for manufacturing phosphonium salts of polyenes. The salts are especially suitable as intermediates in carotenoid and retinoid syntheses.

SUMMARY OF THE INVENTION

Compounds of the formula:

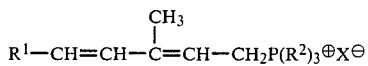

$$R^1-CH=CH-\underset{\underset{CH_3}{|}}{C}=CH-CH_2P(R^2)_3^\oplus X^\ominus \quad\quad I$$

wherein $R^1$ is 2,6,6-trimethyl-1-cyclohexen-1-yl or 2,3,6-trimethylphenyl, either of which is unsubstituted or substituted by a hydroxy group or a protected hydroxy group; $R^2$ is aryl and $X^\ominus$ is an anion;
are produced by hydrogenating a compound of the formula:

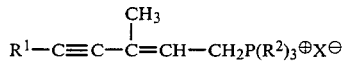

$$R^1-C\equiv C-\underset{\underset{CH_3}{|}}{C}=CH-CH_2P(R^2)_3^\oplus X^\ominus \quad\quad II$$

wherein $R^1$, $R^2$ and $X^\ominus$ are as above,
in an organic or aqueous-organic solvent in the presence of a nickel-, palladium-, platinum-, cobalt-, rhodium-, iridium- or ruthenium-containing catalyst.

The process is suitable as an intermediate step in carotenoid and retinoid syntheses.

The invention is also concerned with all novel compounds, mixtures, processes, uses and devices as herein described.

It has been discovered that the compounds of formula I can be obtained in high yield according to the process provided by the invention. This is surprising, since compounds corresponding to formula I, but without a phosphonium group, hitherto could not be hydrogenated or could be hydrogenated only in unsatisfactory yield. Furthermore, the hydrogenation of acetylenic phosphonium salts of formula I was hitherto not known.

DETAILED DESCRIPTION OF THE INVENTION

In accordance with the invention compounds of the formula:

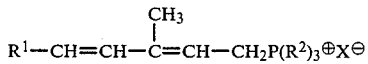

$$R^1-CH=CH-\underset{\underset{CH_3}{|}}{C}=CH-CH_2P(R^2)_3^\oplus X^\ominus \quad\quad I$$

wherein $R^1$ is a 2,6,6-trimethyl-1-cyclohexen-1-yl or 2,3,6-trimethylphenyl group, either of which is unsubstituted or substituted by hydroxy or a protected hydroxy group, $R^2$ is aryl and $X^\ominus$ is an anion,
are manufactured by partially hydrogenating a compound of the formula:

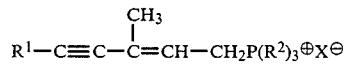

$$R^1-C\equiv C-\underset{\underset{CH_3}{|}}{C}=CH-CH_2P(R^2)_3^\oplus X^\ominus \quad\quad II$$

wherein $R^1$, $R^2$ and $X^\ominus$ are as above,
in an organic or aqueous-organic solvent in the presence of a nickel-, palladium-, platinum-, cobalt-, rhodium-, iridium- or ruthenium-containing catalyst.

As used herein, "lower-alkyl" means straight or branched chain alkyl groups having from 1 to 7 carbon atoms (e.g., methyl, ethyl, n-propyl and isopropyl). "Lower alkoxy" means straight or branched chain alkoxy groups having from 1 to 7 carbon atoms (e.g., methoxy ethoxy and isopropoxy).

"Halogen" or "halide" denotes chlorine, bromine and iodine.

"Aryl" denotes mononuclear and polynuclear aromatic hydrocarbon groups which are unsubstituted or substituted in one or more positions with halogen, nitro, lower alkyl or lower alkoxy. Typical aryl groups includes phenyl, tolyl, benzyl, naphthyl, anthranyl, phenanthranyl, azulyl and the like which can be unsubstituted or substituted with one or more of the aforementioned substituents.

Unless otherwise indicated, all formulae throughout the specification and claims embrace cis and trans isomeric mixtures as well as pure cis and pure trans isomers.

As used herein the term "protected hydroxy group" denotes any conventional groups used for protecting hydroxy functions. Examples of protected hydroxy groups are ether, ester, acetal and the like. The term also includes those groups which can be converted into a hydroxy radical during hydrogenation of compound I. Preferred protected hydroxy groups are alkoxy and acyloxy groups of from 1 to 7 carbon atoms and acetal groups of from 2 to 7 carbon atoms such as methoxy, ethoxy, acetoxy, (2-methoxy-2-propyl)oxy and benzyloxy. Methoxy and acetoxy are especially preferred.

Hydroxy or a protected hydroxy group which is optionally present in $R^1$ is preferably positioned in the 4-position of the cyclohexenyl or phenyl group of $R^1$. Especially preferred groups denoted by $R^1$ are 2,6,6-trimethyl-1-cyclohexen-1-yl, 4-hydroxy-2,6,6-trimethyl-1-cyclohexen-1-yl, 2,3,6-trimethylphenyl and 4-methoxy-2,3,6-trimethylphenyl.

$R^2$ represents an aryl group conventional in phosphonium salts such as phenyl, tolyl and the like, especially phenyl.

$X^\ominus$ embraces all anions conventional to phosphonium salts such as chloride, bromide, perchlorate, hydrogen sulphate and the like. X preferably represents chlorine or bromine.

It has been discovered that the compounds of formula I can be obtained in high yield according to the process provided by the invention. This is surprising, since compounds corresponding to formula I, but without a phosphonium group, hitherto could not be hydrogenated or could be hydrogenated only in unsatisfactory yield. Furthermore, the hydrogenation of acetylenic phosphonium salts of formula I was hitherto not known.

The inventive process can be carried out with a conventional homogeneous or heterogeneous hydrogenation catalyst. Heterogeneous catalysts are preferred. Heterogeneous catalysts can be used with or without a carrier material. Any conventional carrier material may be used. Suitable carrier materials are, for example, carbon, siliceous earth, barium sulphate, calcium carbonate and the like.

The catalysts may be in the form of a pure metal or a metal compound. Suitable metals are nickel, palladium, platinum, cobalt, rhodium, iridium and ruthenium. Preferred metallic catalysts are platinum, nickel, palladium and especially Raney-nickel. Typical metal compound catalysts are metal halides, metal oxides or metal organophosphine halides. More specifically, palladium chloride, palladium oxide, platinum oxide or tris-(triphenylphosphine) rhodium chloride, which is also known as the Wilkinson catalyst, may be used.

Furthermore, the term catalyst as used herein also embraces mixed catalysts (i.e. those containing two or more of the aforementioned metals or metal compounds) and catalysts doped with foreign (i.e. noncatalyzing) metals. Foreign metals especially suitable for doping are heavy metals, such as those conventionally added to hydrogenation catalysts. For example, the heavy metals are molybdenum, palladium, cobalt, ruthenium, vanadium, manganese, lead, copper, chromium, iron, zirconium and the like.

Furthermore, the selectivity of the catalyst may be increased by the use of catalyst deactivation agents or poisons (catalyst modifying agents). The term catalyst as used throughout this application thus embraces catalysts which have been selectively deactivated with a catalytic deactivating agent. Suitable catalyst deactivators are the compounds which are conventionally used for deactivating hydrogenation catalysts including sulphur compounds. 1,2-Bis(2-hydroxyethylthio)ethane is a preferred catalyst deactivator.

In the instant inventive process, metallic catalysts which can be doped with foreign metals and/or which can be deactivated by catalyst deactivating agents are preferably employed. An especially preferred catalyst is Raney-nickel which may or may not be doped with molybdenum, ruthenium, manganese, palladium, cobalt, lead, copper or vanadium and/or which may be selectively deactivated with 1,2-bis2-(hydroxyethylthio)ethane.

The amount of catalyst used is not critical and can therefore vary widely. Moreover, the catalyst can generally be used several times.

In accordance with the invention, the hydrogenation can be carried out in any conventional organic solvent used in catalytic hydrogenation. The solvent can also include water so as to form an aqueous-organic solvent. Suitable organic solvents or organic components of aqueous-organic solvents are alcohols, esters, ethers, ketones and the like. However, ketones are generally also reduced under the reaction conditions employed. Examples of preferred solvents are methanol, ethanol and mixtures of water with one or more of methanol, ethanol, methyl acetate, tetrahydrofuran or acetone. Methanol is especially suitable, since the hydrogenation proceeds especially rapidly and selectively in this solvent and methanol is an excellent solvent for the phosphonium salt.

The temperature and pressure at which the hydrogenation is carried out are not critical. The optimum conditions vary according to the educt, catalyst and solvent used. However, the hydrogenation is generally carried out at a temperature of about 0° C. or to about 100° C., preferably about 20° C. to about 50° C., and a hydrogen pressure of about 0.1 to about 100 bar. The hydrogenation can be carried out in particular also at room temperature (about 23° C.) and under normal pressure (about 1 atm). At temperatures lower than room temperature a somewhat higher yield is generally obtained, whereas at temperatures higher than room temperature the hydrogenation time generally is shortened distinctly but the selectivity of the catalyst nevertheless remains good.

The product compounds of formula I may be an isomer mixture, especially when an isomer mixture has been used as the starting material. If desired, pure isomers can be obtained from the mixture in a known manner. For example, the pure isomers within formula I can be obtained from the mixture by conventional isomerization. More specifically, the isomer mixture can be reacted with any conventional heavy metal compound utilized in isomerization, in the presence of a conventional trace acid, or by heating and/or by recrystallization. Typical heavy metal compounds which may be used in such isomerization are palladium(II) compounds, e.g. palladium(II)acetate. Typical trace acids are sulfuric acid, hydrochloric acid and the like.

The starting materials of formula II are known or can be prepared from known compounds by conventional techniques.

In particular the compounds of the formula:

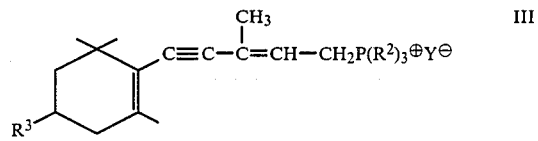

wherein Y is halogen, $R^2$ is an aryl and $R^3$ is hydroxy or a protected hydroxy group,
can, however, also be prepared by reacting a compound of the formula:

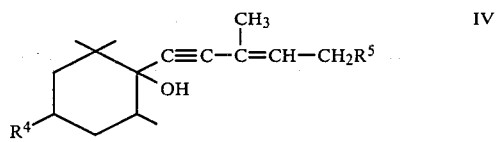

wherein $R^4$ and $R^5$ individually are hydroxy or a protected hydroxy group,
first with a hydrogen halide and then subsequently with a triarylphosphine.

This process can be carried out under the conditions which are usually used for the conversion of an allylic alcohol into a halide and the further conversion thereof into a phosphonium salt. The reaction of compound IV with a hydrogen halide is preferably carried out by the addition of an aqueous hydrogen halide solution at about 0 to about 70° C. The reaction with a triarylphosphine is preferably carried out under reflux conditions. Phenyl is the preferred aryl group denoted by $R^2$.

In compound III, Y is preferably chlorine or bromine. In compound III and/or compound IV, $R^3$, $R^4$ and $R^5$ signify hydroxy or a protected hydroxy group. $R^4$ and $R^5$ also embrace, of course, protected hydroxy groups which are converted into hydroxy, under the reaction conditions.

The compounds of formula I can be converted into carotenoids or retinoids in a known manner.

The invention is also concerned with all novel compounds, mixtures, processes, uses and devices as herein described.

The invention is illustrated by the following Examples. HPLC signifies High Pressure Liquid Chromatography. The working-up of the crude products and the separation of isomers or isomerizations were generally not optimized. Unless otherwise stated, percentages and ratios relating to solvent mixtures are expressed in volume, purity data determined by gas chromatography are expressed in area % and the remaining percentages and ratios are expressed in weight. Temperatures are in degrees Celsius (°C.), normal pressure is about 1 atmosphere and room temperature is about 23° C. Unless indicated otherwise, the Examples were carried out as written.

EXAMPLE 1

A solution of 56.0 g of 90% (4R,2ZE)-[5-(4-hydroxy-2,6,6-trimethyl-1-cyclohexen-1-yl)-3-methyl-2-penten-4-ynyl]triphenylphosphonium bromide (isomer ratio Z/E=62.5:37.2) in 1 liter of methanol was hydrogenated in a hydrogenation flask provided with a gasification stirrer in the presence of 15 g of Raney-nickel (methanol-moist) at 22° C. and 0.1 bar of hydrogen until the hydrogen uptake came to a standstill and less than 2% of educt were present (7.5 hours; hydrogen uptake about 2.2 l). The solution was separated off from the catalyst and the catalyst was washed in the hydrogenation flask with 250 ml of methanol (by suspension and decantation) and, after the addition of 2 g of fresh Raney-nickel, used for a further hydrogenation (as described above). The hydrogenation time required with the recycled catalyst was 22 hours. The hydrogenation solutions of the two batches were filtered and evaporated to dryness in a rotary evaporator (40° C./15 mbar), there being obtained as the residue 96.4 g of a solid brown foam of (4R,2ZE,4Z)-[5-(4-hydroxy-2,6,6-trimethyl-1-cyclohexen-1-yl)-3-methyl-2,4-pentadienyl]triphenylphosphonium bromide (chemical yield 84% in accordance with HPLC). 1200 ml of ethyl acetate were added dropwise while stirring at room temperature to a solution of the residue in 500 ml of methylene chloride, the product crystallizing. The suspension was stirred at room temperature for 2 hours and left to stand in a refrigerator for 16 hours in order to complete the crystallization. The yellow-brown crystals were filtered off, washed with 200 ml of methylene chloride/ethyl acetate (volume ratio 1:2) and dried at 60° C./15 mbar for 8 hours, there being obtained 65.0 g (64.8%) of (4R,2ZE,4Z)-[5-(4-hydroxy-2,6,6-trimethyl-1-cyclohexen-1-yl)-3-methyl-2,4-pentadienyl]triphenylphosphonium bromide; melting point 188°–190° C., $[\alpha]_D^{20} = -18.5°$ (c=1, chloroform). In accordance with HPLC the product contained 63.5% of the (2Z,4Z)-isomer and 31.0% of the (2E,4Z)-isomer.

EXAMPLE 2

A solution of 3.09 g of (4R,2ZE)-[5-(4-hydroxy-2,6,6-trimethyl-1-cyclohexen-1-yl)-3-methyl-2-penten-4-ynyl[triphenylphosphonium chloride (isomer ratio Z/E=9:91) in 240 ml of methanol was hydrogenated in a sulphonation flask provided with a gasification stirrer in the presence of 1.8 g of water-moist Raney-nickel at room temperature and normal pressure for 2 hours (hydrogen uptake about 190 ml). The catalyst was filtered off and washed with 20 ml of methanol. The filtrate was evaporated at 40° C/15 mbar in a rotary evaporator. The resulting crude product of (4R,2ZE,4Z)-[5-(4-hydroxy-2,6,6-trimethyl-1-cyclohexen-1-yl)-3-methyl-2,4-pentadienyl]triphenylphosphonium chloride [chemical yield 91.7%, isomer ratio (2E,4Z)/(2Z,4Z)=80.2:11.5 in accordance with HPLC] was dissolved in 20 ml of methylene chloride and crystallized by the dropwise addition of 60 ml of ethyl acetate. After standing at 0° C. for 16 hours, the pale beige crystals were filtered off, washed with a small amount of methylene chloride/ethyl acetate (volume ratio 1:2) and dried, there being obtained 2.27 g (73.2%) of phosphonium salt containing 85.9% of the (4R,2E,4Z)-isomer and 11.4% of the (4R,2Z,4Z)-isomer; melting point 203°–205° C. By three-fold recrystallization from methylene chloride/ethyl acetate there was obtained 560 mg of pure [5-(4-hydroxy-2,6,6-trimethyl-1-cyclohexen-1-yl)-3-methyl-2,4-pentadienyl]triphenylphosphonium chloride (consisting of 97.3% of the (4R,2E,4Z)-isomer and 2.7% of the (4R,2Z,4Z)-isomer in accordance with HPLC]; melting point 210°–212° C.; $[\alpha]_D^{20} = -25.4°$ (c=1, chloroform).

EXAMPLE 3

In a manner analogous to Example 2, a solution of 7.72 g of (4R,2Z)-[5-(4-hydroxy-2,6,6-trimethyl-1-cyclohexen-1-yl)-3-methyl-2-penten-4-ynyl]triphenylphosphonium chloride [containing 0.4% of the (4R,2E)-isomer] in 480 ml of methanol was hydrogenated in the presence of 3.6 g of water-moist Raney-nickel. About 600 ml of hydrogen were taken up within 4.5 hours. The crude product (7.28 g), which contained 82.4% of (4R,2Z,4Z)-[5-(4-hydroxy-2,6,6-trimethyl-1-cyclohexen-1-yl)-3-methyl-2,4-pentadienyl]triphenylphosphonium chloride in accordance with HPLC, obtained after filtration and evaporation was dissolved in 30 ml of methylene chloride and crystallized at room temperature by the dropwise addition of 75 ml of ethyl acetate. After standing at 0° C. for 16 hours, the suspension was filtered and the product was washed with 20 ml of methylene chloride/ethyl acetate (volume ratio 1.2) and dried, to obtain 5.31 g of 92.9% (4R,2Z,4Z)-[5-(4-hydroxy-2,6,6-trimethyl-1-cyclohexen-1-yl)-3-methyl-2,4-pentadienyl]triphenylphosphonium chloride as pale grey crystals having a melting point of 112°–114° C.; yield 68.4%. A repeated recrystallization from methylene chloride/ethyl acetate yielded 2.7 g of colourless crystals of melting point 114°–116° C., $[\alpha]_D^{20} = -18.3°$ (c—1, chloroform), which contained the pure (4R,2Z,4Z)-isomer and 10.6% of methylene chloride.

EXAMPLE 4

In a manner analogous to Example 2, a solution of 3.26 g of [5-(2,6,6-trimethyl-1-cyclohexen-1-yl)-3-methyl-2-penten-4-ynyl]triphenylphosphonium bromide (isomer ratio E/Z=3:1) in 240 ml of methanol was hydrogenated in the presence of 1.8 g of water-moist Raney-nickel. 198 ml of hydrogen were taken up within 6 hours. The crude product (3.2 g) of (2ZE,4Z)-[5-(2,6,6-trimethyl-1-cyclohexen-1-yl)-3-methyl-2,4-pentadienyl]triphenylphosphonium bromide [chemical yield 86%, isomer ratio (2E,4Z)/(2Z,4Z)=65:21 in accordance with HPLC] obtained after filtration and evaporation was recrystallized at 0° C. from 30 ml of tetrahydrofuran. The white crystals were washed twice with 10 ml of cold tetrahydrofuran each time and dried at 40° C./15 mbar overnight, there being obtained 1.9 g (58%) of product [containing 77% of the (2E,4Z)-isomer and 18% of the (2Z,4Z)-isomer in accordance with HPLC]; melting point 180°–182° C. Two-fold recrystalisation from methylene chloride/tetrahydrofuran yielded 1.2 g of the (2E,4Z)-isomer as white crystals of melting point 183°–185° C.

EXAMPLE 5

In a manner analogous to Example 2, a solution of 3.24 g of [3-methyl-5-(2,3,6-trimethylphenyl)-2-penten-4-ynyl]triphenylphosphonium bromide (isomer ratio Z/E=1:2) in 240 ml of methanol was hydrogenated in the presence of 1.8 g of water-moist Raney-nickel. 150 ml of hydrogen were taken up within 7 hours. The crude product (3.3 g) of (2E,4EZ)-[3-methyl-5-(2,3,6-trimethylphenyl)-2,4-pentadienyl]triphenylphosphonium bromide [chemical yield 98%, isomer ratio (2E,4Z)/(2E,4E)=84:14 in accordance with HPLC] obtained after filtration and evaporation was taken up in 10 ml of methyl chloride and crystallized by the addition of 60 ml of ethyl acetate and evaporation of the methylene chloride. The suspension was stirred at room temperature for 4 hours, then filtered and the crystals were washed with a small amount of cold ethyl acetate and dried up to constant weight at room temperature and 0.01 mbar, there being obtained 1.60 g (50%) of pure product [containing 85.9% of the (2E,4Z)-isomer and 14.1% of the (2E,4E)-isomer in accordance with HPLC] as beige crystals of melting point 85°–86° C. By two-fold recrystallization from methylene chloride/ethyl acetate there was obtained the pure (2E,4Z)-isomer in the form of white crystals; melting point 154°–157° C. (greatly dependent on the rate of heating).

EXAMPLE 6

In a manner analogous to Example 2, a solution of 3.42 g of (Z)-[5-(4-methoxy-2,3,6-trimethylphenyl)-3-methyl-2-penten-4-ynyl]triphenylphosphonium bromide in 240 ml of methanol was hydrogenated in the presence of 1.8 g of water-moist Raney-nickel. 188 ml of hydrogen were taken up within 28 hours. The crude product (3.4 g), which contained 89.4% of (2Z,4Z)-[5-(4-methoxy-2,3,6-trimethylphenyl)-3-methyl-2,4-pentadienyl]triphenylphosphonium bromide (yield 89%), obtained after filtration and evaporation was dissolved in 20 ml of methylene chloride and crystallized by the dropwise addition of 50 ml of ethyl acetate while stirring. The suspension was left to stand at 0° C. overnight, filtered and the product, washed with a small amount of ethyl acetate/methylene chloride (volume ratio 5:1), was dried at 40°C./0.01 mbar. There were obtained 1.8 g of 99.6% (2Z,4Z)-[5-(4-methoxy-2,3,6-trimethylphenyl)-3-methyl-2,4-pentadienyl]triphenylphosphonium bromide as white crystals of melting point 202°–204° C.; yield 52.5%.

EXAMPLE 7

The experiments compiled in Table 1 were carried out in a manner analogous to Example 2, in each case 3.36 g of (4R,2ZE)-[5-(4-hydroxy-2,6,6-trimethyl-1-cyclohexen-1-yl)-3-methyl-2-penten-4-ynyl]triphenylphosphonium bromide (isomer ratio E/Z=73.27) in 240 ml of methanol being hydrogenated using different catalysts to give (4R,2ZE,4Z)-[5-(4-hydroxy-2,6,6-trimethyl-1-cyclohexen-1-yl)-3-methyl-2,4-pentadienyl]triphenylphosphonium bromide. In Table 1 p signifies the pressure, T signifies the temperature and t signifies the hydrogenation time. In the case of experiments which were carried out under elevated pressure a measurement of the amount of hydrogen consumed was not possible for technical reasons. The composition of the hydrogenation product was determined by means of HPLC (area percentage).

TABLE 1

| Catalyst | p (bar) | T (°C.) | t (h) | H₂-uptake (mol-eq.) | Composition of the hydrogenation product (%) | | | | |
|---|---|---|---|---|---|---|---|---|---|
| | | | | | Educt | | Product | | |
| | | | | | (2E) | (2Z) | (2E,4Z) | (2Z,4Z) | Total |
| 3.6 g Ni/siliceous earth (52%) | 90 | 50 | 22 | | 2.3 | 0.4 | 62.3 | 21.1 | 83.4 |
| 1.0 g Pd/C (5%) | 1 | 22 | 25 | 1.2 | 4.2 | 23.7 | 41.1 | 20.2 | 61.3 |
| 1.0 g Pd/BaSO₄ (5%) | 1 | 22 | 24 | 1.4 | 0.4 | 13.2 | 58.1 | 17.1 | 75.2 |
| 1.0 g Pd/siliceous earth (5%) | 1 | 22 | 20 | 1.3 | 2.3 | 19.5 | 54.2 | 15.0 | 69.2 |
| 0.3 g PdCl₂/C (pre-hydrogenated) | 1 | 23 | 25 | 1.4 | 7.7 | 19.0 | 17.8 | 39.4 | 57.2 |
| 4.0 g Pt/C (5%); | 90 | 50 | 4 | | — | 0.3 | 53.9 | 31.5 | 85.4 |
| 2.0 g Ru/C (5%) | 90 | 50 | 24 | | 21.4 | 23.4 | 29.2 | 10.8 | 40.0 |
| 2.0 g Ir/C (5%) | 90 | 50 | 17 | | 5.2 | 21.4 | 43.5 | 14.2 | 57.7 |
| 1.0 g Rh/C (5%) | 1 | 24 | 18 | | 17.8 | 29.2 | 34.8 | 12.4 | 57.2 |
| 3.6 g Raney-Co | 90 | 50 | 6 | | 21.3 | 36.2 | 32.0 | 8.1 | 40.1 |

EXAMPLE 8

The experiments (a)–(e) compiled in Table 2 were carried out in a manner analogous to Example 2. In experiment (a) 3.09 g of (4R,2ZE)-[5-(4-hydroxy-2,6,6-trimethyl-1-cyclohexen-1-yl)-3-methyl-2-penten-4-ynyl]triphenylphosphonium chloride (isomer ratio Z/E=9:91) were hydrogenated to give (4R,2ZE,4Z)-[5-hydroxy-2,6,6-trimethyl-1-cyclohexen-1-yl)-3-methyl-2,4-pentadienyl]triphenylphosphonium chloride and in each of experiments (b)–(e) 3.36 g of (4R,2ZE)-[5-(4-hydroxy-2,6,6-trimethyl-1-cyclohexen-1-yl)-3-methyl-2-penten-4-ynyl]triphenylphosphonium bromide (isomer ratio Z/E=27:73) were hydrogenated to give (4R,2ZE,4Z)-[5-(4-hydroxy-2,6,6-trimethyl-1-cyclohexen-1-yl)-3-methyl-2,4-pentadienyl]triphenylphosphonium bromide. All experiments were carried out in the presence of 1.8 g of Raney-nickel at 20° C. and under normal pressure. t signifies the hydrogenation time. The composition of the hydrogenation product was determined by means of HPLC (area percentage).

TABLE 2

| Experiment | Solvent (total 240 ml) | t (h) | Composition of the hydrogenation product (%) | | | | |
|---|---|---|---|---|---|---|---|
| | | | Educt | | Product | | |
| | | | (2E) | (2Z) | (2E,4Z) | (2Z,4Z) | Total |
| (a) | Ethanol | 25 | — | 2.2 | 77.5 | 14.6 | 92.1 |
| (b) | Methanol + 100 ml water | 19 | — | 8.7 | 59.6 | 23.8 | 83.4 |

TABLE 2-continued

| Experiment | Solvent (total 240 ml) | t (h) | Composition of the hydrogenation product (%) | | | | |
|---|---|---|---|---|---|---|---|
| | | | Educt | | Product | | |
| | | | (2E) | (2Z) | (2E,4Z) | (2Z,4Z) | Total |
| (c) | Methyl acetate + 20 ml water | 22 | — | 1.0 | 61.6 | 28.3 | 89.9 |
| (d) | Tetrahydrofuran + 35 ml water | 22 | — | 0.2 | 61.8 | 28.3 | 90.1 |
| (e) | Acetone + 35 ml water | 2 | 1.2 | 8.7 | 59.5 | 23.8 | 84.3 |

EXAMPLE 9

In each experiment compiled in Table 3, 3.36 g of (4R,2ZE)-[5-(4-hydroxy-2,6,6-trimethyl-cyclohexen-1-yl)-3-methyl-2-penten-4-ynyl]triphenylphosphonium bromide (isomer ratio E/Z=49.1:50.9) in 240 ml of methanol were hydrogenated to give (4R,2ZE,4Z)-[5-(4-hydroxy-2,6,6-trimethyl-1-cyclohexen-1-yl)-3-methyl-2,4-pentadienyl]triphenylphosphonium bromide in a manner analogous to Example 2 under the conditions given in Table 3. All experiments were carried out in the presence of 1.8 g of Raney-nickel doped with foreign metal and under 1 bar of hydrogen. T signifies the reaction temperature and t signifies the hydrogenation time. The composition of the hydrogenation product was determined by means of HPLC (area percentage), the total corresponding to approximately the chemical yield. In all experiments the hydrogenation product no longer contained (2E)-educt in accordance with HPLC. The working-up of the hydrogenation product was carried out in a manner analogous to Example 2.

EXAMPLE 11

In a manner analogous to Example 2, a solution of 3.26 g of [5-(2,6,6-trimethyl-1-cyclohexen-1-yl)-3-methyl-2-penten-4-ynyl]triphenylphosphonium bromide (isomer ratio E/Z=3:1) in 220 ml of methyl acetate and 20 ml of water was hydrogenated in the presence of 1.8 g of water-moist Raney-nickel. 185 ml of hydrogen were taken up within 24 hours. The crude product (3.3 g) of (2ZE,4Z)-[5-(2,6,6-trimethyl-1-cyclohexen-1-yl)-3-methyl-2,4-pentadienyl]triphenylphosphonium bromide [chemical yield 76%, isomer ratio (2E,4Z)/(2Z,4Z)=61:15 in accordance with HPLC], which still contained 10.8% of educt, obtained after filtration and evaporation was recrystallized at 0° C. from 40 ml of tetrahydrofuran. The white crystals were washed twice with 10 ml of cold tetrahydrofuran each time and dried at 60° C./15 mbar overnight, there being obtained 1.4 g (42.9%) of product [containing 79% of the (2E,4Z)-isomer and 16% of the (2Z,4Z)-isomer in accordance with HPLC]; melting point 176°–178° C.

TABLE 3

| Catalyst 1.8 g of Raney-Ni doped with | T (0°) | t (h) | $H_2$-uptake (mol-eq.) | Composition of the hydrogenation product (%) | | | | Isolated product | |
|---|---|---|---|---|---|---|---|---|---|
| | | | | Educt | Product | | | Yield | Purity |
| | | | | (2Z) | (2E,4Z) | (2Z,4Z) | Total | (%) | (%) |
| 1.2% Mo | 22 | 5 | 1.35 | — | 39.1 | 48.8 | 87.9 | 54.7 | 100 |
| 1.0% Pd | 23 | 3 | 1.40 | — | 39.5 | 45.6 | 85.1 | 59.0 | 93.8 |
| 5.0% Co | 22–23 | 17 | 1.45 | 1.5 | 40.1 | 44.5 | 84.6 | 62.1 | 98.1 |
| 1.0% Ru | 21–23 | 8 | 1.37 | — | 38.3 | 47.3 | 85.6 | 68.3 | 89.0 |
| 1.0% V | 22–24 | 12 | 1.37 | 0.4 | 38.0 | 44.9 | 82.9 | 55.9 | 99.1 |
| 2.5% Co + 1.5% Mo | 22–23 | 24 | 1.22 | 14.2 | 39.2 | 37.7 | 76.9 | 72.0 | 82.8 |
| 2% Mn | 24 | 3.25 | 1.39 | 2.2 | 40.0 | 45.3 | 85.3 | 57.5 | 97.3 |
| 2% Pb | 24 | 3 | 1.35 | 1.4 | 39.5 | 45.0 | 84.5 | 48.1 | 99.2 |
| 2% Cu | 22–23 | 3 | 1.39 | — | 39.3 | 45.0 | 84.3 | 48.1 | 99.6 |

EXAMPLE 10

In a manner analogous to Example 2, a solution of 2.0 g of [5-(2,6,6-trimethyl-1-cyclohexen-1-yl)-3-methyl-2-penten-4-ynyl]triphenylphosphonium bromide (isomer ratio E/Z=3:1) in 150 ml of methanol was hydrogenated in the presence of 1.1 g of Raney-nickel doped with 1% palladium. 112 ml of hydrogen were taken up within 2 hours. The crude product (2.0 g) of (2ZE,4Z)-[5-(2,6,6-trimethyl-1-cyclohexen-1-yl)-3-methyl-2,4-pentadienyl]triphenylphosphonium bromide [chemical yield 71%, isomer ratio (2E,4Z)/(2Z,4Z)=57:14 in accordance with HPLC], which still contained 17% of educt, obtained after filtration and evaporation was recrystallized at 0° C. from 40 ml of tetrahydrofuran. The white crystals were washed twice with 10 ml of cold tetrahydrofuran each time and dried at 60° C./15 mbar overnight, there being obtained 0.9 g (44.8%) of product [containing 81% of the (2E,4Z)-isomer and 13.5% of the (2Z,4Z)-isomer in accordance with HPLC]; melting point 182°–184° C.

EXAMPLE 12

A solution of 2.0 g of [5-(2,6,6-trimethyl-1-cyclohexen-1-yl)-3-methyl-2-penten-4-ynyl]triphenylphosphonium bromide (isomer ratio E/Z=3:1) in 150 ml of methanol was hydrogenated in a sulphonation flask provided with a gasification stirrer in the presence of 2.5 g of platinum/carbon (5%) at 50° C. under pressure (90 bar). The crude product (2.0 g) of (2ZE,4Z)-[5-(2,6,6-trimethyl-1-cyclohexen-1-yl)-3-methyl-2,4-pentadienyl]triphenylphosphonium bromide [chemical yield 86%, isomer ratio (2E,4Z)/(2Z,4Z)=65:21 in accordance with HPLC], which still contained 4% of educt, obtained after filtration and evaporation was recrystallized at 0° C. from 40 ml of tetrahydrofuran. The white crystals were washed twice with 10 ml of cold tetrahydrofuran each time and dried at 60° C./15 mbar overnight, there being obtained 0.95 g (47.5%) of product [containing 76% of the (2E,4Z)-isomer and 19% of the (2Z,4Z)-isomer in accordance with HPLC]; melting point 177°–179° C.

EXAMPLE 13

In a manner analogous to Example 2, a solution of 3.36 g of (4R,2ZE)-[5-(4-hydroxy-2,6,6-trimethyl-1-cyclohexen-1-yl)-3-methyl-2-penten-4-ynyl]triphenylphosphonium bromide (isomer ratio Z/E=2.8:97.2) in 240 ml of methanol was hydrogenated in the presence of 1.8 g of moist Raney-nickel doped with 1.2% of molybdenum. 168 ml of hydrogen were taken yp within 9 hours. The crude product of (4R,2ZE, 4Z)-[5-(4-hydroxy-2,6,6-trimethyl-1-cyclohexen-1-yl)-3-methyl-2,4-pentadienyl]triphenylphosphonium bromide [chemical yield 93.3%, isomer ratio (2E,4Z)/(2Z,4Z)=87.1:6.2 in accordance with HPLC] obtained after filtration and evaporation was dissolved in 15 ml of methylene chloride and crystallized by the dropwise addition of 40 ml of ethyl acetate. After standing at 0° C. for 16 hours, the pale beige crystals were filtered off, washed with a small amount of methylene chloride/ethyl acetate (volume ratio 1:2) and dried, there being obtained 2.55 g (75.7%) of product [containing 91.6% of the (2E,4Z)-isomer and 5.5% of the (2Z,4Z)-isomer in accordance with HPLC]; melting point 203°-204° C.

EXAMPLE 14

In a manner analogous to Example 2, a solution of 3.36 g of (4R,2E)-[5-(4-hydroxy-2,6,6-trimethyl-1-cyclohexen-1-yl)-3-methyl-2-penten-4-ynyl]triphenylphosphonium bromide [containing 0.6% of the (2Z)-isomer] in 240 ml of methanol was hydrogenated in the presence of 1 g of palladium/barium sulphate (5%). 200 ml of hydrogen were taken up within 2 hours. The crude product of (4R,2ZE,4Z)-[5-(4-hydroxy-2,6,6-trimethyl-1-cyclohexen-1-yl)-3-methyl-2,4-pentadienyl]triphenylphosphonium bromide [chemical yield 90.3%, isomer ratio (2E,4Z)/(2Z,4Z)=81.8:8.5 in accordance with HPLC] obtained after filtration and evaporation was dissolved in 12 ml of methylene chloride and crystallized by the dropwise addition of 20 ml of ethyl acetate. After standing at 0° C. for 16 hours, the pale beige crystals were filtered off, washed with a small amount of methylene chloride/ethyl acetate (volume ratio 1:2) and dried, there being obtained 2.20 g (65.9%) of product [containing 89.6% of the (2E,4Z)-isomer and 9.8% of the (2Z,4Z)-isomer in accordance with HPLC]; m.p. 198°-199° C.

EXAMPLE 15

A solution of 30.0 g of (4R,2E)-[5-(4-hydroxy-2,6,6-trimethyl-1-cyclohexen-1-yl)-3-methyl-2-penten-4-ynyl]triphenylphosphonium bromide in 1 liter of methanol was hydrogenated in a hydrogenation flask provided with a gasification stirrer in the presence of 10 g of Raney-nickel at 22° C. and 0.1 bar of hydrogen. 1.3 l of hydrogen were taken up within 3.5 hours. The crude product of (4R,2ZE,4Z)-[5-(4-hydroxy-2,6,6-trimethyl-1-cyclohexen-1-yl)-3-methyl-2,4-pentadienyl]triphenylphosphonium bromide [chemical yield 94.2%, isomer ratio (2E,4Z)/(2Z,4Z)=87.2:7.0 in accordance with HPLC] obtained after filtration and evaporation was crystallized from 15 ml of methanol and 190 ml of ethyl acetate. After standing at 0° C. for 16 hours, the crystals were filtered off, washed with a small amount of methanol/ethyl acetate (volume ratio 1:9) and dried, there being obtained 21.3 g (73.5%) of pure product [consisting of 94.4% of the (2E,4Z)-isomer and 5.6% of the (2Z,4Z)-isomer in accordance with HPLC]; melting point 207°-208° C., $[\alpha]_D^{20} = -23.4°$ (c=1, chloroform).

EXAMPLE 16

In a manner analagous to Example 2, a solution of 3.42 g of (Z)-[5-(4-methoxy-2,3,6-trimethylphenyl)-3-methyl-2-penten-4-ynyl]triphenylphosphonium bromide in 240 ml of methanol was hydrogenated in the presence of 1.8 g of palladium/barium sulphate (5%). 188 ml of hydrogen were taken up within 2 hours. The crude product (3.4 g) of (2Z,4Z)-[5-(4-methoxy-2,3,6-trimethylphenyl)-3-methyl-2,4-pentadienyl]triphenylphosphonium bromide (chemical yield 54.6% in accordance with HPLC) obtained after filtration and evaporation was dissolved in 20 ml of methylene chloride and crystallized by the dropwise addition of 50 ml of ethyl acetate while stirring. The suspension was left to stand at 0° C. overnight and filtered. The crystals were washed with a small amount of ethyl acetate/methylene chloride (volume ratio 5:1) and dried at room temperature/0.01 mbar. There was thus obtained 1.0 g of 94.9% (2Z,4Z)-[5-(4-methoxy-2,3,6-trimethylphenyl)-3-methyl-2,4-pentadienyl]triphenylphosphonium bromide; m.p. 202°-205° C.

EXAMPLE 17

A suspension of 126.2 g of (1RS,2R,4R,2E)-5-(1,4-dihydroxy-2,6,6-trimethyl-1-cyclohexyl)-3-methyl-2-penten-4-yn-1-ol in 1 liter of methylene chloride was cooled to 0° C. in a sulphonation flask provided with a stirrer, thermometer, dropping funnel with pressure balance and argon headpiece and then treated while stirring within 15 minutes with 283 ml of 48% aqueous hydrogen bromide solution. The violet-black mixture was stirred vigorously at 0° C. until complete reaction was achieved in accordance with thin-layer chromatography (about 1–1.5 hours). For the working-up, three separating funnels S$_1$–S$_3$ were each charged with 250 ml of semi-saturated aqueous sodium chloride solution. Now, the reaction mixture and then three 100 ml portions of methylene chloride were passed in succession through the separating funnels S$_1$–S$_3$. The separated organic phase was dried over 50 g of sodium sulphate, the suspension was suction filtered and the filter residue was rinsed with 100 ml of methylene chloride. The filtrates were concentrated to a volume of about 1.2 l in a rotary evaporator under a water-jet vacuum and immediately added dropwise to 144.2 g of crystalline triphenylphosphine, which was placed in a sulphonation flask provided with a stirrer, thermometer and reflux condenser with fitted gasification connection, so that the exothermic reaction could be held at controlled reflux (addition time 1 hour). The mixture was subsequently stirred until the reaction was complete (about 2 hours), the product crystallizing out partially. The suspension was now virtually concentrated in a rotary evaporator under a water-jet vacuum to give 450 g of a brown crystallizate. This was dissolved in 100 ml of methanol at reflux and the solution was treated with 1.2 l of ethyl acetate within 1 hour without a cooling bath while stirring mechanically. The product crystallization occurred after the addition of about 800 ml of ethyl acetate. The suspension was cooled to −15° C. overnight, then suction filtered and the product was rinsed very thoroughly three times with 500 ml of ethyl acetate, there being obtained beige crystals. The still solvent-moist crystallizate was dissolved in 100 ml of methanol at reflux and the solution was treated with 1.2

1 of ethyl acetate within 30 minutes without a cooling bath while stirring mechanically. The product crystallization occurred after the addition of about 270 ml of ethyl acetate. The suspension was stored at −15° C. overnight, then suction filtered and the product was rinsed very thoroughly three times with 500 ml of ethyl acetate and dried up to constant weight at 40° C. in a drying oven under a water-jet vacuum. In this manner there were obtained 151.6 g (54.2%) of (4R,2ZE)-[5-(4-hydroxy-2,6,6-trimethyl-1-cyclohexen-1-yl)-3-methyl-2-penten-4-ynyl]triphenylphosphonium bromide [consisting of 37.4% of the (2E)-isomer and 62.6% of the (2Z)-isomer] as a pale beige powder; melting point 199°–200° C., $[\alpha]_D = -47.2°$ (0.25%, chloroform). The mother liquors of the two aforementioned crystallizations were worked-up and crystallized in the manner described above from in each case 100 ml of methanol and in each case 1 liter of ethyl acetate. There were thus obtained 55.7 g (19.9%) of (4R,2E)-[5-(4-hydroxy-2,6,6-trimethyl-1-cyclohexen-1-yl)-3-methyl-2-penten-4-ynyl]triphenylphosphonium bromide as a pale beige powder; melting point 205°–207° C., $[\alpha]_D = -44.5°$ (1.0%, chloroform). The last mother liquor, which still contained product, was not worked up. The total yield was 207.3 g (74.1%).

EXAMPLE 18

12.0 g of Raney-nickel, 132.0 mg of 1,2-bis(2-hydroxyethylthio)ethane and 200 ml of methanol were placed in a sulphonation flask provided with a gasification stirrer and pre-hydrogenated at room temperature for 40 minutes. Subsequently, a solution of 24.4 g of (2E)-[5-(2,6,6-trimethyl-1-cyclohexen-1-yl)-3-methyl-2-penten-4-ynyl]triphenylphosphonium bromide in 400 ml of methanol was added thereto and the mixture was hydrogenated at room temperature under normal pressure for 15.5 hours (hydrogen consumption 1150 ml). The mixture was filtered and the residue was rinsed well with methanol. The filtrate was concentrated at about 40° C. (bath temperature) in a rotary evaporator under a vacuum and the residue was dried briefly in a high vacuum. The crude product (27.3 g) obtained was dissolved in 20 ml of methylene chloride and the solution was treated dropwise with 300 ml of ethyl acetate while seeding and stirred at room temperature for a further 4 hours. The precipitate was filtered off under suction, washed well with ethyl acetate and dried in a high vacuum. There were thus obtained 19.5 g (79.6%) of (2E,4Z)-[5-(2,6,6-trimethyl-1-cyclohexen-1-yl)-3-methyl2,4-pentadienyl]triphenylphosphonium bromide as white crystals.

EXAMPLE 19

A suspension of 46.6 g of water-moist Raney-nickel and 518 mg of 1,2-bis(2-hydroxyethylthio)ethane in 1 l of methanol was pre-hydrogenated at 30° C. under normal pressure in a sulphonation flask provided with a gasification stirrer. Subsequently, a solution of 320 g of (4R,2E)-[5-(4-hydroxy-2,6,6-trimethyl-1-cyclohexen-1-yl)-3-methyl-2-penten-4-ynyl]triphenylphosphonium chloride in 2.1 l of methanol was added thereto and the mixture was hydrogenated at 40° C. and 1.1 bar of hydrogen. 15.6 l of hydrogen were taken up within 5 hours. The catalyst was filtered off and the filtrate was concentrated to a weight of 575 g. The product was crystallized by slowly pouring in 9.6 l of ethyl acetate. The suspension was stirred at room temperature for 2 hours and filtered. The crystals were washed with a small amount of methanol/ethyl acetate and dried at 60° C./0.01 mbar, there being obtained 272.2 g (84.7%) of [5-(4-hydroxy-2,6,6-trimethyl-1-cyclohexen-1-yl)-3-methyl-2,4-pentadienyl]triphenylphosphonium chloride (containing 97% of the (4R,2E,4Z)-isomer and 2% of the (4R,2Z,4Z)-isomer in accordance with HPLC) of melting point 211°–212° C. and $[\alpha]_D^{20} = -26.2°$ (c=1, chloroform).

EXAMPLE 20

In a manner analogous to that described in Example 19, 200 g of (4R,2E)-[5-(4-hydroxy-2,6,6-trimethyl-1-cyclohexen-1-yl)-3-methyl-2-penten-4-ynyl]triphenylphosphonium chloride were hydrogenated at 40° C. and 1.1 bar of hydrogen in the presence of 58 g of Raney-nickel which was water-moist and pre-treated with 650 mg of 1,2-bis(2-hydroxyethylthio)ethane. After cooling, the solution which was above the catalyst was sucked off, filtered and worked-up as described in Example 19. This procedure was repeated twice more, there being used each time the catalyst residue of the preceding cycle, 2 l of methanol, 11 g of fresh Raney-nickel and 200 g of educt and the hydrogenation being carried out at 40° C. and 1.1 bar of hydrogen. The respective hydrogenation time t and the yield of crystalline [5-(4-hydroxy-2,6,6-trimethyl-1-cyclohexen-1-yl)-3-methyl-2,4-pentadienyl]triphenylphosphonium chloride as well as its content of the (4R,2E,4Z)-isomer in accordance with HPLC and the $[\alpha]_D^{20}$ values (c=1, chloroform) are given in Table 4.

TABLE 4

| | t | Yield | (4R,2E,4Z)-isomer | $[\alpha]_D^{20}$ |
|---|---|---|---|---|
| 1st cycle | 1.5h | 143.4 g | 95.3% | −26.2° |
| 2nd cycle | 1.5h | 167.5 g | 95.6% | −26.1° |
| 3rd cycle | 2.5h | 188.7 g | 97.2% | −26.3° |

EXAMPLE 21

A solution of 200 g of (4R,2Z)-[5-(4-hydroxy-2,6,6-trimethyl-1-cyclohexen-1-yl)-3-methyl-2-penten-4-ynyl]triphenylphosphonium chloride in 2 l of methanol was hydrogenated under normal pressure in the presence of 58 g of the catalyst pre-treated according to Example 19 at 19°–28° C. for 6 hours and then at 40° C. for 11 hours. Working-up in a manner analogous to Example 19 gave 159.4 g (79.4%) of white crystals which in addition to (4R,2Z,4Z)-[5-(4-hydroxy-2,6,6-trimethyl-1-cyclohexen-1-yl)-3-methyl-2,4-pentadienyl]triphenylphosphonium chloride still contained 5.5% of methanol and 0.2% of ethyl acetate; melting point 123°–127° C., $[\alpha]_D^{20} = -20.4°$ (c=1, chloroform).

What is claimed is:

1. A process for producing a compound of the formula:

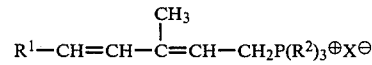

wherein $R^1$ is 2,6,6,-trimethyl-1-cyclohexen-1-yl or 2,3,6-trimethylphenyl, either of which is unsubstituted or substituted with hydroxy or a protected hydroxy group; $R^2$ is aryl and $X^\ominus$ is an anion, which process comprises selectively hydrogenating a compound of the formula:

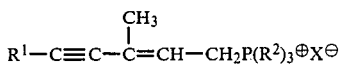

wherein $R^1$, $R^2$ and $X^\ominus$ are as above,
said compounds I and II being in any of their various cis and trans sterioisomeric forms and mixtures thereof, in an organic solvent in the presence of a catalyst which is a metal or metal compound, said metal being nickel, palladium, platinum, cobalt, rhodium, iridium or ruthenium.

2. The process of claim 1 wherein $R^1$ is 2,6,6-trimethyl-1-cyclohexen-1-yl or 2,3,6-trimethylphenyl either of which is unsubstituted or substituted with hydroxy, methoxy or acetoxy.

3. The process of claim 2 wherein $R^1$ is 2,6,6-trimethyl-1-cyclohexen-1-yl, 4-hydroxy-2,6,6-trimethyl-1-cyclohexen-1-yl, 2,3,6-trimethylphenyl or 4-methoxy-2,3,6-trimethylphenyl.

4. The process of claim 1 wherein $R^2$ is phenyl.

5. The process of claim 1 wherein $X^\ominus$ is chloride, bromide, perchlorate or hydrogen sulfate.

6. The process of claim 5 wherein $X^\ominus$ is chloride or bromide.

7. The process of claim 1 wherein the catalyst is one or more of said metals.

8. The process of claim 7, wherein the metal catalyst is platinum, nickel, palladium or Raney-nickel.

9. The process of claim 8 wherein the metal catalyst is Raney-nickel.

10. The process of claim 1 wherein the catalyst is one or more of said metal compounds.

11. The process of claim 10 wherein the metal compound catalyst is a metal halide, metal oxide or metal organophosphine halide.

12. The process of claim 11 wherein the metal compound catalyst is palladium chloride, palladium oxide, platinum oxide or tris(triphenylphosphine) rhodium chloride.

13. The process of claim 1 wherein the catalyst is heterogeneous.

14. The process of claim 13 wherein the catalyst further comprises a heavy metal.

15. The process of claim 14 wherein the heavy metal is molybdenum, palladium, cobalt, ruthenium, vanadium, manganese, lead, copper, chromium, iron, or zirconium.

16. The process of claim 14 wherein the catalyst is Raney-nickel and the heavy metal is molybdenum, ruthenium, manganese, palladium, cobalt, lead, copper or vanadium.

17. The process of claim 13 wherein said catalyst is selectively deactivated by a catalytic deactivation agent.

18. The process of claim 17 wherein the catalytic deactivation agent is 1, 2-bis(2-hydroxyethylthio)ethane.

19. The process of claim 17 wherein the catalyst is Raney-nickel which is selectively deactivated with 1,2-bis(2-hydroxyethylthio) ethane.

20. The process of claim 1 wherein the organic solvent is an alcohol, ester, ether or ketone.

21. The process of claim 20, wherein the organic solvent is methanol or ethanol.

22. The process of claim 1 wherein the organic solvent further comprises water so as to form an aqueous-organic solvent.

23. The process of claim 22 wherein the aqueous-organic solvent is a mixture of water and one or more of methanol, ethanol, methyl acetate, tetrahydrofuran or acetone.

24. A process for producing a compound of the formula:

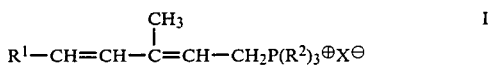

wherein $R^1$ is 2,6,6-trimethyl-1-cyclohexen-1-yl, 2,3,6-trimethylphenyl, 4-hydroxy-2,6,6-trimethyl-1-cyclohexen-1-yl, or 4-methoxy-2,3,6-trimethylphenyl; $R^2$ is phenyl and $X^\ominus$ is chloride or bromide;
which process comprises selectively hydrogenating a compound of the formula:

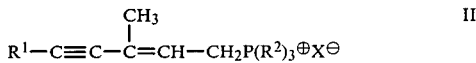

wherein $R^1$, $R^2$ and $X^\ominus$ are as above, said compounds I and II being in any of their varios cis and trans stereoisomeric forms and mixtures thereof, in an organic solvent in the presence of catalytic amounts of Raney-nickel.

* * * * *